US008759099B2

(12) United States Patent
Tanemura et al.

(10) Patent No.: US 8,759,099 B2
(45) Date of Patent: Jun. 24, 2014

(54) PANCREATIC ISLET SEPARATION METHOD, AND PROTECTIVE SOLUTION FOR PROTECTING PANCREATIC ISLET TISSUE

(75) Inventors: Masahiro Tanemura, Kure (JP); Yoshiki Sawa, Suita (JP); Akira Myoui, Suita (JP); Toshinori Ito, Suita (JP); Masaki Mori, Suita (JP); Yuichiro Doki, Suita (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 13/808,390

(22) PCT Filed: Jul. 13, 2011

(86) PCT No.: PCT/JP2011/065997
§ 371 (c)(1),
(2), (4) Date: Mar. 13, 2013

(87) PCT Pub. No.: WO2012/008496
PCT Pub. Date: Jan. 19, 2012

(65) Prior Publication Data
US 2013/0177986 A1    Jul. 11, 2013

(30) Foreign Application Priority Data
Jul. 13, 2010  (JP) .................................. 2010 159053

(51) Int. Cl.
*C12N 5/00* (2006.01)
(52) U.S. Cl.
USPC ......................................... 435/381; 435/378
(58) Field of Classification Search
USPC ................................................ 435/381, 378
See application file for complete search history.

(56) References Cited

U.S. PATENT DOCUMENTS

| 4,797,213 A | 1/1989 | Parisius et al. |
| 2008/0038823 A1 | 2/2008 | Matsumoto et al. |

FOREIGN PATENT DOCUMENTS

| JP | 62-265981 A | 11/1987 |
| WO | WO 2006/068226 A1 | 6/2006 |

OTHER PUBLICATIONS

Ricordi et al. (Automated Method for Isolation of Human Pancreatic Islets. Diabetes (1988) vol. 37: 413-420).*
Masuko et al., "Sequential change of several parameters and the role of ulinastatin administration in acute pancreatitis," The Japanese Journal of Acute Medicine, 1995, 19(13):1945-1952, with English summary.
Miyamoto et al., "Improved large-scale isolation of breeder porcine islets: Possibility of harvesting from nonheart-beating donor," Cell Transplantation, 1998, 7(4):397-402.
Omura et al., "Significant improvement of islet yield and viability in islet isolation with modified ET-Kyoto solution (ET-Kyoto/neutrophil elastase inhibitor)," Journal of Japan Surgical Society, May 25, 2011, 112(1-2):751, PS-142-1, with English translation.
Ota et al., "The Effect of Sivelestat Sodium Hydrate on Ischemic Reperfusion Injury of the Segmental Pancreatic Autotransplantation in the Swine," American Journal of Transplantation, May 2007, 7(Supp.2):510, Abstract 1412.
Rose et al., "An Evaluation of the Activation of Endogeneous Pancreatic Enzymes During Human Islet Isolations," Transplantation Proceedings, 2003, 35(7):2455-2457.
Yamano et al., "Protective effect of the combined treatment of pancreatic and neutrophil elastase inhibitors on acute pancreatitis elicited by lipopolysaccharide in rats given intraductal injection of taurocholate plus trypsin," Naunyn-Schmeideberg's Arch. Pharmacol., 1998, 357:558-564.
Harris et al., "A Novel Neutrophil Elastase Inhibitor Prevents Elastase Activation and Surface Cleavage of the Epithelial Sodium Channel Expressed in *Xenopus laevis* Oocytes," J. Biol. Chem., Jan. 5, 2007 (published online Nov. 7, 2006), 282(1):58-64.
Kuraki et al,. "A Novel Oral Neutrophil Elastase Inhibitor (ONO-6818) Inhibits Human Neutrophil Elastase-induced Emphysema in Rats," Am. J. Respir. Crit. Care Med., 2002, 166:496-500.
Machida et al., "Significant Improvement in Islet Yield and Survival With Modified ET-Kyoto Solution: ET-Kyoto/Neutrophil Elastase Inhibitor," Cell Transplantation, 2013, 22(1):159-173.
Matsumoto et al., "Estimation of Donor Usability for Islet Transplantation in the United States With the Kyoto Islet Isolation Method," Cell Transplantation, 2009, 18:549-556.
Noguchi et al., "Pancreas Preservation by the Two-Layer Method: Does it Have a Beneficial Effect Compared With Simple Preservation in University of Wisconsin Solution?" Cell Transplantation, 2009, 18(5-6):497-503.

(Continued)

*Primary Examiner* — Karen Cochrane Carlson
*Assistant Examiner* — Natalie Moss
(74) *Attorney, Agent, or Firm* — Foley & Lardner LLP

(57) ABSTRACT

The disclosed islet isolation method comprises: an injection step of injecting a preservation solution into the pancreatic duct of an excised pancreas; a preservation step of immersing the pancreas into an immersion fluid for preservation; a digestion step of breaking down the pancreas to provide pancreatic tissue; and a purification step of immersing the pancreatic tissue in a purification solution to provide islets. The digestion step consists of: an enzyme injection step of injecting an enzyme solution containing a digestion enzyme into the pancreas; a digestion initiation step of activating the digestion enzyme; a digestion termination step of inactivating the digestion enzyme; and a collection step of collecting the broken-down pancreatic tissue. The islet isolation method is characterized in that, by adding a neutrophil elastase inhibitor to the system before the digestion initiation step, the neutrophil elastase inhibitor is present inside the pancreas at the time point of starting the digestion initiation step. By using the above method and a protective solution which can be used in the method, islets having a size and shape suitable for transplantation can be obtained in high yields.

13 Claims, 10 Drawing Sheets

(56) References Cited

OTHER PUBLICATIONS

Noguchi et al., "Comparison of Trypsin Inhibitors in Preservation Solution for Islet Isolation," Cell Transplantation, 2009, 18(5-6):541-547.

Ono et al. "The effect of selective neutrophil elastase inhibitor on pancreatic islet yields and functions in rat with hypercytokinemia," Annals of Transplantation: Quarterly of the Polish Transplantation Society, Oct.-Dec. 2011, 16(4):99-106.

Yao et al., "Protective effect of Ulinastatin in rat islet isolation," Chin. J. Organ Transplant, Dec. 2005, 26(12):732-734, with English abstract on first page.

\* cited by examiner

PANCREATIC ISLET SEPARATION METHOD, AND PROTECTIVE SOLUTION FOR PROTECTING PANCREATIC ISLET TISSUE

TECHNICAL FIELD

The present invention relates to a method for isolating transplantable islets from the pancreas and a protective solution for protecting pancreatic tissue used for the isolation method.

BACKGROUND ART

Radical treatments of type 1 diabetes include, for example, pancreas transplantation from a brain-dead donor. The pancreas transplantation has a significant efficacy such as enabling insulin independence by single transplantation. However, the transplantation has a problem of placing a large burden on the body of recipients because it involves a complicated surgery and revascularization, and also, it has the possibility of inducing complications. Accordingly, attention has been focusing on islet transplantation as a new radical treatment of diabetes in recent years. The islet transplantation is a method which involves isolating islets, which are tissues secreting insulin and glucagon as hormones regulating blood sugar, from the pancreas and transplanting the isolated islets into the liver through the portal vein. The transplanted islets are engrafted at the end of the portal vein in the liver, which can secrete insulin.

Whereas conventional pancreas transplantation is a surgical procedure involving extensive invasiveness, the islet transplantation has less surgical stress on the body of recipients and is safe compared to the pancreas transplantation because it requires only a procedure involving leaving a catheter in the portal vein and transplanting islets in the same manner as drip infusion. The islet transplantation is also a kind of cell transplantation unlike other organ transplantations; thus, the semi-permanent frozen storage of islets therefore is possible. In addition, the islet transplantation has the advantage of not requiring it to take the trouble to excise cells even if rejection occurs, because the transplanted islets themselves are absorbed.

However, the islet transplantation has the disadvantage of shortage of islets suitable for transplantation because of the technical difficulty in isolation only of islet cells from the pancreas. As a result, a plurality of transplantations are necessary until insulin independence is achieved, requiring pancreas donations from 2.6 donors on average for one recipient. Accordingly, it is a challenge how to obtain many islets of good quality from the pancreas.

To overcome this challenge, various methods for isolating islets have previously been studied. For example, Patent Document 1 discloses a method for isolating islets, comprising injecting a protective solution containing a protease inhibitor into the pancreatic duct in advance. In the method for isolating islets, the protease inhibitor is used to improve the yield of the islets.

For conventional methods for isolating islets, the cause of not providing islets of sufficient quality and yield is considered to be that endogenous enzymes derived from the exocrine pancreas present in the pancreas are activated by the excision of the pancreas and damage pancreatic tissue, as disclosed in Non Patent Document 1; the above method for isolating islets of Patent Document 1 contemplates the improvement of the quality and yield of the islets by inhibiting the activity of the endogenous enzymes. Examples of the enzymes derived from the exocrine pancreas are trypsin, pancreas-derived elastase, and chymotrypsin; the above Patent Document 1 uses urinastatin, which specifically inhibits trypsin.

Patent Document 1 describes that the appropriate protection of islet tissue by a protease inhibitor results in the increased yield of islets. However, conventional methods often cause the physical damage of islet cells, such as being torn off, during isolation, and have not stably provided islets having a size and shape enough to secrete insulin after transplantation to necessary yields. Also, the urinastatin used as a protease inhibitor in Patent Document 1 has a problem of posing a high risk on a living body and lacking in safety because it is a biological preparation obtained using human urine as a raw material.

RELATED ART DOCUMENTS

Patent Documents

Patent Document 1: International Publication No. WO 2006/068226

Non-Patent Documents

Non Patent Document 1: Transplantation Proceedings, 2003, Vol. 35, no. 7, 2455-7

SUMMARY OF THE INVENTION

Problem to be Solved by the Invention

Accordingly, an object of the present invention is to provide a method for isolating islets in high yields, which are capable of providing islets of shapes and sizes suitable for transplantation, and a protective solution for protecting islet.

Means to Solve the Problem

The present inventors, in making the present invention, have newly found that donor's neutrophils infiltrate into the excised pancreas and increase in number when being passed through a step of digestion and further that neutrophil elastase released from these neutrophils damages the pancreas. Accordingly, the present inventors have focused on the point that the damage of the pancreas can be efficiently suppressed by inhibiting the action of the neutrophil elastase, thereby accomplishing the present invention.

The present invention relates to the followings.

[1] A method for isolating islets, comprising:
a digestion step of breaking down an excised pancreas to provide pancreatic tissue, and
a purification step of immersing the pancreatic tissue in a purification solution to provide islets,
wherein the digestion step comprises:
an enzyme injection step of injecting an enzyme solution containing a digestive enzyme into the inside of the pancreas;
a digestion initiation step of activating the digestive enzyme;
a digestion termination step of inactivating the digestive enzyme; and
a collection step of collecting the broken down pancreatic tissue,
wherein a neutrophil elastase inhibitor (provided that a case of it being a trypsin Inhibitor is excluded) is added before the digestion initiation step so that the neutrophil elastase inhibitor is present in the inside of the pancreas at the time point of starting the digestion initiation step.

[2] The method for isolating islets according to [1], further comprising before the digestion step an injection step of injecting a preservation solution into the pancreatic duct of an excised pancreas and/or a preservation step of immersing the pancreas in an immersion fluid for preservation.

[3] The method for separating islets according to [2], wherein the preservation solution and the immersion fluid do not contain a neutrophil elastase inhibitor.

[4] The method for isolating islets according to [1] to [3], wherein the addition of the neutrophil elastase inhibitor is performed by adding the neutrophil elastase inhibitor to the enzyme solution.

[5] The method for isolating islets according to [1] to [3], wherein the addition of the neutrophil elastase inhibitor is performed by adding the neutrophil elastase inhibitor to the enzyme solution and the purification solution.

[6] The method for isolating islets according to [2], wherein the addition of the neutrophil elastase inhibitor is performed by adding the neutrophil elastase inhibitor to all of the preservation solution, the immersion fluid, the enzyme solution, and the purification solution.

[7] The method for isolating islets according to any one of [4] to [6], wherein the concentrations of the neutrophil elastase inhibitor in the preservation solution, the immersion fluid, the enzyme solution, and the purification solution are 2 to 200 μM.

[8] A protective solution for protecting the pancreatic tissue from the action of elastase released from neutrophils having infiltrated into pancreatic tissue, wherein the protective solution comprises a neutrophil elastase inhibitor (provided that a case of it being a trypsin inhibitor is excluded).

[9] The protective solution according to [8], wherein the concentration of the neutrophil elastase inhibitor in the protective solution is 2 to 200 μM.

As used herein, the protective solution means a preservation solution, an immersion fluid, an enzyme solution, a purification solution, or the like used in the method for isolating islets according to the present invention, added with a neutrophil elastase inhibitor.

Effect of the Invention

According to the present invention, islets of shapes and sizes suitable for transplantation can be obtained in high yields by the method for isolating the islets.

MODE OF CARRYING OUT THE INVENTION

Figure 1:
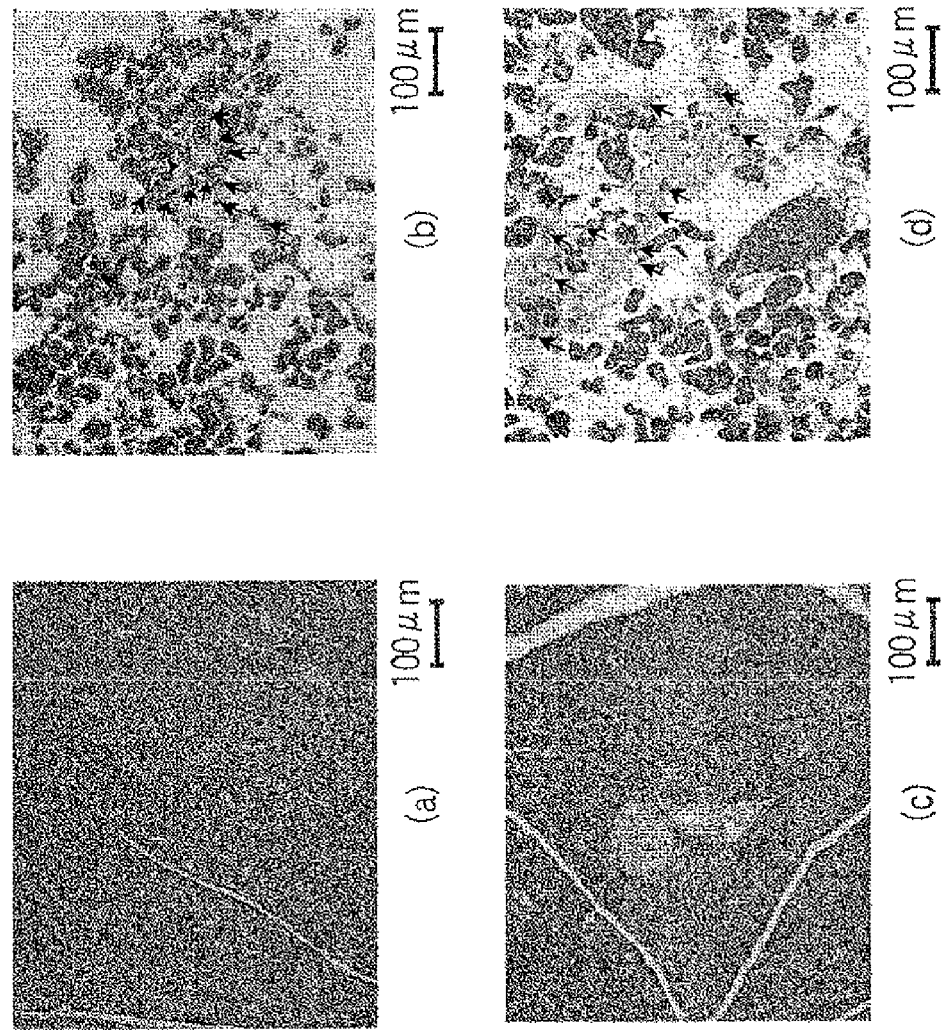
FIG. 1 is a series of photographs ((a) to (d)) showing degrees of infiltration of neutrophils into pancreas.

The islet isolation method of the present invention is described below.

The method for isolating islets according to the present invention comprises (1) an "injection step" of injecting a preservation solution into the pancreatic duct, (2) a "preservation step" of immersing pancreas in an immersion fluid for preservation, (3) a "digestion step" of braking down the pancreas, and (4) a "purification step" of purifying islets from the pancreatic tissue obtained by the breaking-down. In addition, the digestion step consists of the steps: an "enzyme injection step" of injecting an enzyme solution into the pancreatic duct of the pancreas for swelling; a "digestion initiation step" of initiating digestion to break down the pancreas; a "digestion termination step" of terminating the further digestion of the pancreatic tissue; and a "collection step" of collecting and optionally washing and concentrating the broken down pancreatic tissue. The present invention is characterized in that a neutrophil elastase inhibitor is present in the inside of the pancreas at least at the time point of starting the operation of the digestion initiation step among the above steps.

Subsequently, each step in the islet isolation method of the invention of the present application is described.

(1) Injection Step

The injection of a preservation solution into the pancreatic duct is performed as a first step of the islet isolation method. The preservation solution may be injected, for example, by inserting a catheter into the pancreatic duct. The injection pressure may be controlled using a pump. The number of the inserted catheters is preferably one. The leak of the solution injected into the pancreatic duct can be reduced and the organ damage can be minimized by using only one catheter.

The preservation solution has an osmotic pressure of 270 to 450 mOsm/l, preferably 300 to 400 mOsm/l. This range of the osmotic pressure enables the pancreatic tissue to be prevented from swelling or shrinking during preservation after injecting the preservation solution into the pancreatic duct. The preservation solution preferably has a pH of about 7 to 8 to prevent the acidic degradation, etc. of cells and tissue.

The preservation solution injected into the pancreatic duct includes an organ preservation solution. The organ preservation solution may be properly selected from known solutions used for protecting or preserving tissues. For example, but not limited to, UW solution, ET-Kyoto solution, M-Kyoto solution (M-Kyoto solution refers to ET-Kyoto solution containing Miraclid (registered trade name, from Mochida Pharmaceutical Co., Ltd., general name: urinastatin), HTK solution, Euro-Collins solution, and Celsior solution are used. ET-Kyoto solution is particularly preferably used.

A solution that is the preservation solution described above added with a neutrophil elastase inhibitor (called a protective solution) may be used for injection into the pancreatic duct in this step. The neutrophil elastase inhibitor may be, for example, Elaspol (registered trade name, from Ono Pharmaceutical Co., Ltd., general name: sivelestat); however, it is not particularly limited provided that it is an agent having the effect of inhibiting neutrophil elastase.

The amount of the neutrophil elastase inhibitor added to the preservation solution is properly determined depending on the type of the inhibitor within the range in which the present invention is worked. For example, when Elaspol is used, the content of Elaspol per L of the preservation solution is 2 to 200 μmol, preferably 5 to 100 μmol, more preferably 20 μmol.

The preservation solution also preferably contains trehalose. The containing of trehalose further increases the effect of protecting the pancreatic tissue, providing islets more suitable for transplantation. The trehalose may be α,α-trehalose, α,β-trehalose, β,β-trehalose, or a mixture thereof. Preferably, α,α-trehalose is used. The amount of the trehalose contained in the preservation solution is 0 to 400 mmol, preferably 50 to 240 mmol, particularly preferably 80 to 160 mmol in 1,000 ml of the preservation solution.

The concentration of potassium contained in the preservation solution is preferable low. Specifically, the amount of potassium per 1,000 ml of the preservation solution is 4 to 50 mM, preferably 10 to 50 mM. The low concentration of potassium can make the preservation solution quickly spread into every corner of the tissue without contracting the vessels of the pancreas. The preservation solution goes around every corner of the tissue to increase the effect of protecting the pancreatic tissue. Thus, the lower concentration of potassium contained in the preservation solution provides islets more suitable for transplantation.

The preservation solution may further contain other ingredients as long as the advantages of the present invention are not impaired. Other ingredients include, but not limited to, electrolytes, carbohydrates, amino acids, vitamins, and drugs.

(2) Preservation Step

As a second step in the islet isolation method, the pancreas in which the preservation solution is injected into the pancreatic duct is immersed in an immersion fluid for preservation. As the preservation methods, a simple immersion method using an organ preservation solution alone or a two-layer method may be used. The preservation using the two-layer method is a method which involves placing a perfluorocarbon solution (PFC) and an organ preservation solution in a container to form two layers, in which an organ is then placed, followed by preserving the organ while supplying oxygen into the container. Thus, the immersion fluid in the present invention means, for example, but not limited to, an organ preservation solution when the simple immersion method is used, and PFC and the organ preservation solution when the two-layer method is used. Any solution capable of preserving pancreas can be used as the immersion fluid of the present invention. When the two-layer method is used, the ratio of the perfluorocarbon solution (PFC) to the organ preservation solution is preferably 1:1 by volume. The supply of oxygen is preferably performed for at least 30 minutes. The preservation of the pancreas by the two-layer method can maintain the viability of the pancreatic tissue at a high level.

This preservation step is necessary when a time interval is present between the operation of excising the pancreas from a donor and the operation of isolating islets from the excised pancreas; however, it can be omitted when the time interval is not present and the immediate shift to the operation of isolating islets can be made.

Non-limiting examples of the organ preservation solution used include UW solution, ET-Kyoto solution, M-Kyoto solution, HTK solution, Euro-Collins solution, and Celsior solution.

A solution that is the immersion fluid described above added with a neutrophil elastase inhibitor (called a protective solution) is also preferably used for preservation in this step. The neutrophil elastase inhibitor can be not only injected into the pancreatic duct in the injection step but also used in the preservation step to make the neutrophil elastase inhibitor go around the pancreatic tissue. As a result, the action of neutrophil elastase can be inhibited in a wide area, enabling the damage of islets to be effectively suppressed.

Examples of the neutrophil elastase inhibitor used here include Elaspol; however, the inhibitor is not particularly limited provided that it is an agent having the effect of inhibiting neutrophil elastase. The amount of the neutrophil elastase inhibitor contained in a liquid for immersion preservation is 2 to 200 μmol, preferably 5 to 100 μmol, more, preferably 20 μmol per L of the immersion fluid when Elaspol is used.

The organ preservation solution also preferably contains trehalose. The containing of trehalose further increases the effect of protecting the pancreatic tissue, providing islets more suitable for transplantation. The trehalose may be α,α-trehalose, α,β-trehalose, β,β-trehalose, or a mixture thereof. Preferably, α,α-trehalose is used. The amount of the trehalose contained in the organ preservation solution is 0 to 400 mmol, preferably 50 to 240 mmol, particularly preferably 80 to 160 mmol in 1,000 ml of the organ preservation solution.

The concentration of potassium contained in the organ preservation solution is preferable low. Specifically, the amount of potassium per 1,000 ml of the organ preservation solution is 4 to 50 mM, preferably 10 to 50 mM. The low concentration of potassium can appropriately preserve the pancreas without contracting the vessels of the pancreas. Thus, the lower concentration of potassium contained in the organ preservation solution provides islets more suitable for transplantation.

The organ preservation solution may further contain other ingredients as long as the advantages of the present invention are not impaired. Other ingredients include, but not limited to, electrolytes, carbohydrates, amino acids, drugs, and vitamins.

The organ preservation solution has an osmotic pressure of 270 to 450 mOsm/l, preferably 300 to 400 mOsm/l. This range of the osmotic pressure enables the pancreatic tissue to be prevented from swelling or shrinking during the preservation of the organ. The organ preservation solution also preferably has a pH of about 7 to 8 to prevent the acidic degradation, etc. of cells and tissue.

(3) Digestion Step

As a third step in the islet isolation method, a digestive enzyme is injected into the pancreas to break down (digest) the pancreas. Specifically, an enzyme solution having the effect of breaking down pancreas is injected into the pancreatic duct to swell the pancreas (hereinafter referred to as an "enzyme injection step"), followed by activating the enzyme to break down the pancreas (hereinafter referred to as a "digestion initiation step"). Thereafter, the enzyme is inactivated to terminate the digestion (hereinafter referred to as a "digestion termination step"), followed by collecting the broken-down pancreatic tissue (hereinafter referred to as a "collection step").

Examples of the enzyme solution which may be used include, but not limited to, a collagenase solution. Collagenase is an enzyme operative to decompose the collagen connecting the tissues of the pancreas.

A solution that is the enzyme solution added with a neutrophil elastase inhibitor (called a protective solution) is also preferably used for injection into the pancreatic duct in this step. The presence of the neutrophil elastase inhibitor in the digestion step enables the pancreatic tissue to sufficiently contact the neutrophil elastase inhibitor. Thus, the action of neutrophil elastase can be inhibited in a wide area, enabling the damage of islets to be effectively suppressed. For example, when Elaspol is used as a neutrophil elastase inhibitor, the content of Elaspol per L of the protective solution is 2 to 200 μM, preferably 5 to 100 μM, more preferably 20 μM.

When (1) Injection Step and/or (2) Preservation Step is omitted, the enzyme solution preferably contains the preservation solution described in the (1) Injection Step.

The injection of the enzyme solution into the pancreatic duct in the enzyme injection step may be carried out in the same procedure as for the above-described injection of the preservation solution.

The enzyme activation in the digestion initiation step can be performed, for example, by increasing the temperature of the system. Specifically, the pancreas swollen by the injection of collagenase is placed in a chamber, and the route for digestion is filled with the solution to make a closed system. Thereafter, the solution is circulated using a pump, and the solution is warmed to such a temperature that collagenase is activated. The elevated temperature activates the collagenase infiltrated into the pancreatic tissue, which results in dissolving the collagen forming the tissue connecting cells to break down the pancreatic tissue. Collagenase is most activated around 37° C. Thus, when collagenase is brought into action to break down the pancreas, it is necessary to elevate the system temperature to about 37° C.

The digestion termination step is carried out at the time point that cells forming islets retain an aggregated morphology and the exocrine pancreatic tissue dissociates from the periphery of islets. The termination of digestion can be performed by reducing the temperature of the system. Alternatively, it can also be carried out by adding serum protein to inactivate the enzyme. The inactivation by adding serum protein can be carried out, for example, by making the route into an open system and flushing the solution of a room temperature containing human albumin into the route. Flushing the solution of room temperature inactivates the enzyme by reducing the temperature of the system and diluting the enzyme. The enzyme is inactivated by adding serum protein.

After terminating the digestion, the degraded pancreatic tissue is collected as a collection step. The collected pancreatic tissue is preferably subjected to the centrifugation with washing using a centrifugal separator for concentration before purification.

(4) Purification Step

As a fourth step in the islet isolation method, the purification of the pancreatic tissue collected in the preceding step is carried out. The purification is a step of isolating the pancreatic tissue into islets and exocrine pancreatic tissue. The operation of this step is performed using a purification solution containing a density gradient reagent. The islet has a low specific gravity compared to the exocrine pancreatic tissue. This is exploited to place the degraded pancreatic tissue in a purification solution in which a density gradient is formed by the density gradient reagent to isolate the islets and the exocrine pancreatic tissue by a specific gravity centrifugal method.

The density gradient reagent can be properly selected from among those which are each known to be used for the preparation of a density gradient in a solution. Examples thereof which can be used include OptiPrep (from Axis-Shield plc, general name: iodixanol solution), Nycodenz (from Axis-Shield plc, general name: iodixanol powder). The density gradient reagent used here is preferably one capable of preparing a purification solution having low viscosity. The purification solution with lower viscosity enables the more rapid purification. The preferable viscosity range is 5 cp or less, preferably 3 cp or less, more preferably 2 cp or less when the measurement thereof is performed at a measurement temperature of 22° C. by the Brookfield method. The density gradient reagent used is preferably one having a low endotoxin level.

The purification solution is obtained by adding a density gradient reagent to an organ preservation solution. The definition of the organ preservation solution used here is as described in the above step of immersion-preserving the pancreas. Among the organ preservation solutions listed above, those containing trehalose can be used; it is preferable to use ET-Kyoto solution. When an organ preservation solution containing no trehalose is used, trehalose may be added to the purification solution. In this case, α,α-trehalose, α,β-trehalose, β,β-trehalose, or a mixture thereof may be used. Preferably, α,α-trehalose is used. The amount of the trehalose contained in the purification solution is 0 to 400 mmol, preferably 50 to 240 mmol, particularly preferably 80 to 160 mmol in 1,000 ml of the purification solution.

A solution that is the purification solution added with a neutrophil elastase inhibitor (called a protective solution) is preferably used for the operation of this step. The neutrophil elastase activity is also maintained after breaking down the pancreas, which can produce cellular damage. Thus, preferably, the neutrophil elastase inhibitor is also present in the purification step to protect the islets from the cell-damaging action. The neutrophil elastase inhibitor added to the purification solution can provide less damaged islets. The amount of the neutrophil elastase contained in the purification solution is 2 to 200 μmol, preferably 5 to 100 μmol, more preferably 20 μmol per L of the purification solution when Elaspol is used.

The purification solution may further contain other ingredients as long as the advantages of the present invention are not impaired. Other ingredients include, but not limited to, adenosine, dextran, and heparin.

The rate of addition of the density gradient reagent to the organ preservation solution is set by measuring the density of the pancreatic tissue before purification and considering the specific gravities of the density gradient reagent and the organ preservation solution.

The density gradient can be formed by a known method. The density gradient may also be formed using a device such as a continuous density-generating device. Either the continuous density gradient or the non-continuous density gradient is available; however, the continuous density gradient is preferable in view of being capable of collecting more islets.

In the purification step, a series of operations may also be carried out using a blood-cell washing device such as COBE2991. When COBE2991 is used, a density gradient reagent is first exploited to prepare a density gradient in the device; a washed and concentrated degraded pancreatic tissue is placed therein; and it is isolated into islets and exocrine pancreatic tissue by a continuous specific gravity centrifugal method. Then, the solution in the device is collected by each fraction. The fractions are subjected to microscopic examination to determine in which fraction islets are present, and the islets are collected.

The above is the details of the operations in the steps, and among these, the injection step of (1) and the preservation step of (2) are steps performed for the purpose of preventing the deterioration of the excised organ with time. Thus, when islets can be isolated immediately after excising the pancreas, these (1) and/or (2) steps can be properly omitted.

However, when a time interval is present between the organ-excising operation and the islets-isolating operation, such as when the organ is required to be transported to a distance, it is necessary to surely go through the preservation step of (2) without omission. More preferably, it is desired to go through both of the (1) and (2) steps.

The neutrophil elastase inhibitor can be used in all of the steps; however, the neutrophil elastase inhibitor may be added in each step so that it is present in the pancreas at least at the time point of entering into the operation of the digestion initiation step in the digestion step of (3). For example, the addition of the neutrophil elastase inhibitor can be limited only to the enzyme solution injected in the enzyme injection step in the digestion step of (3). The inhibitor may also be added only to the immersion fluid in the preservation step of (2) as a preceding step for the digestion step, and may also be added only to the preservation solution in the injection step of (1) as a preceding step therefor.

According to the above islet isolation method of the present invention, large islets can be obtained compared to those for conventional methods. The islets obtained are not defective, exhibit so high a survival rate in recipients that the size thereof is comparable to the original size thereof in the pancreas, and have a high ability to secrete insulin. From these reasons, the larger islets can be said to be more suitable for transplantation.

In addition, the islets obtained by the method of the present invention are excellent in terms of shape. As shown in Examples to be described later, according to the method of the present invention, islets that are spherical and high in density and have intact pancreatic tissue can be obtained. Such islets have a high ability to secrete insulin and considered to be suitable for transplantation. The islets obtained by the method of the present invention are also high in purity.

According to the method of the present invention, the operation of isolating islets can also be simplified and efficiently performed by more decreasing the frequency of use of an agent such as a neutrophil elastase inhibitor.

According to the present invention, the action of a neutrophil elastase released during the breaking-down of pancreas can be suppressed by a neutrophil elastase inhibitor to provide less damaged islets suitable for transplantation. In other words, according to the present invention, islets having shapes and sizes suitable for transplantation can be obtained in high yields.

EXAMPLES

The present invention is based on the new finding that donor's neutrophils infiltrate into pancreas after excision and increase in number when being passed through a step of digestion. Accordingly, the finding obtained by the inventors is described first. FIG. 1 is a series of photographs showing degrees of infiltration of neutrophils into pancreatic tissue; the following experiment was carried out using pancreas excised from a mouse.

First, mouse pancreas was excised; UW solution or ET-Kyoto solution, which was added with type-IV collagenase, was injected into the pancreatic duct to swell the pancreas; then, a portion of the pancreatic tissue was collected. Then, the swollen pancreas was digested by incubation at 37° C. for 15 minutes, and after digestion, a portion of the pancreatic tissue was again collected. The collected pancreatic tissue was stained with hematoxylin-eosin (HE), and the neutrophils infiltrated into the pancreatic tissue were stained with naphthol-ASD-chroloacetate esterase. Both stained images of the predigested pancreatic tissue and the digested pancreatic tissue were compared with each other.

In FIG. 1,(a) and (c) on the left hand side show the stained images of pancreatic tissue before digestion; (b) and (d) on the right hand side show the stained images of pancreatic tissue after digestion; and the stained images indicated by arrows show activated neutrophils. The upper (a) and (b) show cases where UW solution was used, and the lower (c) and (d) show cases where ET-Kyoto solution was used.

FIGS. 1(a) and 1(c) show that the infiltration of neutrophils is absent in the undigested pancreatic tissue, that is, normal pancreatic tissue before the digestion step. On the other hand, (b) and (d) on the right hand side in FIG. 1 show that the infiltration of neutrophils is present and the number of neutrophils was increased compared to that before digestion, after the digestion step in which the pancreas was broken down with collagenase. The same pancreatic tissue was used in FIGS. 1(a) and 1(b), and in FIGS. 1(c) and 1(d), respectively. Thus, it is probable that neutrophils were already present in the excised pancreas and more neutrophils infiltrated into the pancreatic tissue by the breaking-down of the pancreas through the digestion step.

Neutrophils release neutrophil elastase when activated. It is known that the neutrophil elastase has an important effect of an enzymatic digestion and decomposition of bacteria, etc. having entered a living body under an environment in which an endogenous inhibitor acts, but causes the damage of tissue when the action of the inhibitor is reduced from any cause. Thus, islets are probably damaged when neutrophils are activated in the step of isolating the islets.

Figure 2:
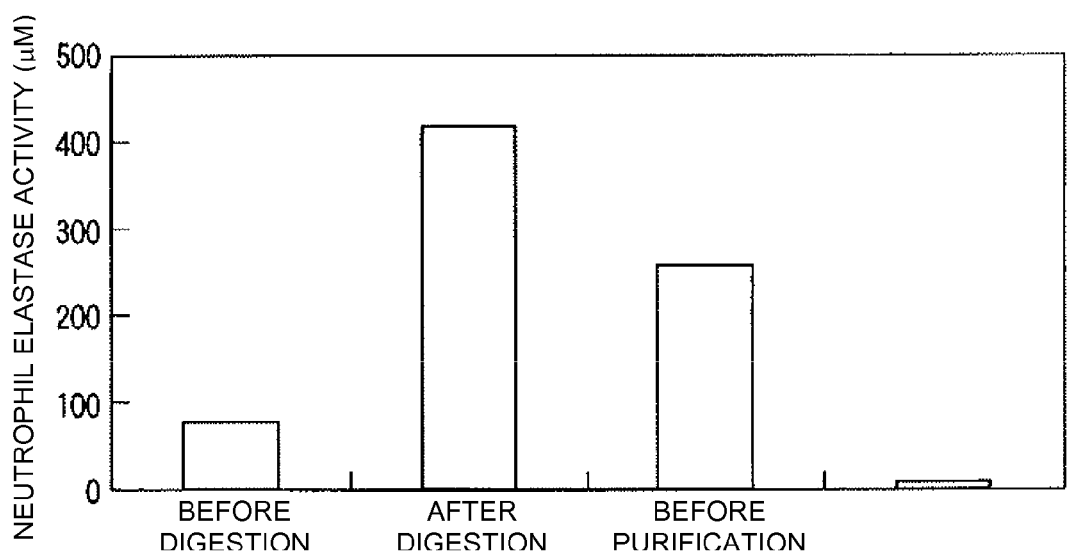
FIG. 2 is a graph showing neutrophil elastase activity in each step of islet isolation.

Accordingly, to know in which situation in the islet isolation step neutrophils are activated, the activity of neutrophil elastase in each step was examined; the results are shown in FIG. 2.

The experiment was carried out using mice. The organ preservation solution used was ET-Kyoto solution. For the measurement of neutrophil elastase activity, the supernatant of the suspension containing pancreatic tissue obtained in each step of the islet isolation was used as a measurement sample; the sample was incubated in a reaction solution containing a neutrophil elastase-specific substrate at 37° C. for 24 hours; and the amount of p-nitroanilide released into the reaction solution was determined using absorbance at a wavelength of 405 nm.

As used herein, the "before digestion" refers to a state in which collagenase, having the effect of breaking down pancreas, was injected into the pancreatic duct to swell the pancreas, that is, after the enzyme injection step and before the digestion initiation step in the invention of the present application. The "after digestion" refers to a state in which the collagenase was activated after swelling the pancreas to break down it, followed by inactivating the collagenase to terminate the digestion, that is, after the digestion termination step and before the collection step in the invention of the present application. The "before purification" refers to a state in which the pancreatic tissue was collected and washed after terminating the digestion, that is, after the collection step and before the purification step in the invention of the present application. The "after purification" refers to a state in which islets were isolated from the exocrine pancreatic tissue using a density gradient reagent, that is, after the purification step in the invention of the present application.

This figure shows that the activity of neutrophil elastase in the pancreas becomes highest at the time point of "after digestion". It also shows that the neutrophil elastase activity is decreased at the time point of "before purification", that is, after the operation of washing the pancreatic tissue, and further the neutrophil elastase activity is more decreased at the time point of "after purification" having passed through the purification step. In other words, the islets are predicted to be most damaged at the time point of "after digestion", and the islets excellent in quality can be obtained efficiently by preventing the damage at this time point.

The present invention is based on the above findings and is characterized in that a neutrophil elastase inhibitor is present in the inside of the pancreas at least at the time point of entering into the digestion initiation step in the digestion step.

The concentration of the neutrophil elastase inhibitor used in the isolation method of the present invention was examined as follows using the extracellular leakage of LDH (lactate dehydrogenase) (indicator for cytotoxicity) as an indicator.

First, mouse islets were cultured in the presence of neutrophil elastase at a concentration of 0.31 to 10 µg/mL and the supernatant was collected after a lapse of a certain time. Subsequently, the remaining mouse islets were homogenized and the islet suspension was collected. LDH contained in the collected supernatant and the islet suspension was measured by using a LDH assay kit to measure absorbance at 562 nm. The optimal concentration of the neutrophil elastase inhibitor was examined by adding 2 to 200 µM of the neutrophil elastase inhibitor, sivelestat, in culturing mouse islets in the presence of various concentrations of neutrophil elastase, and similarly measuring the amount of LDH. The cytotoxicity was expressed as the percentage (%) of the amount of LDH contained in the supernatant in the sum of the amount of LDH contained in the supernatant and the amount of LDH contained in the islet suspension.

Figure 3:
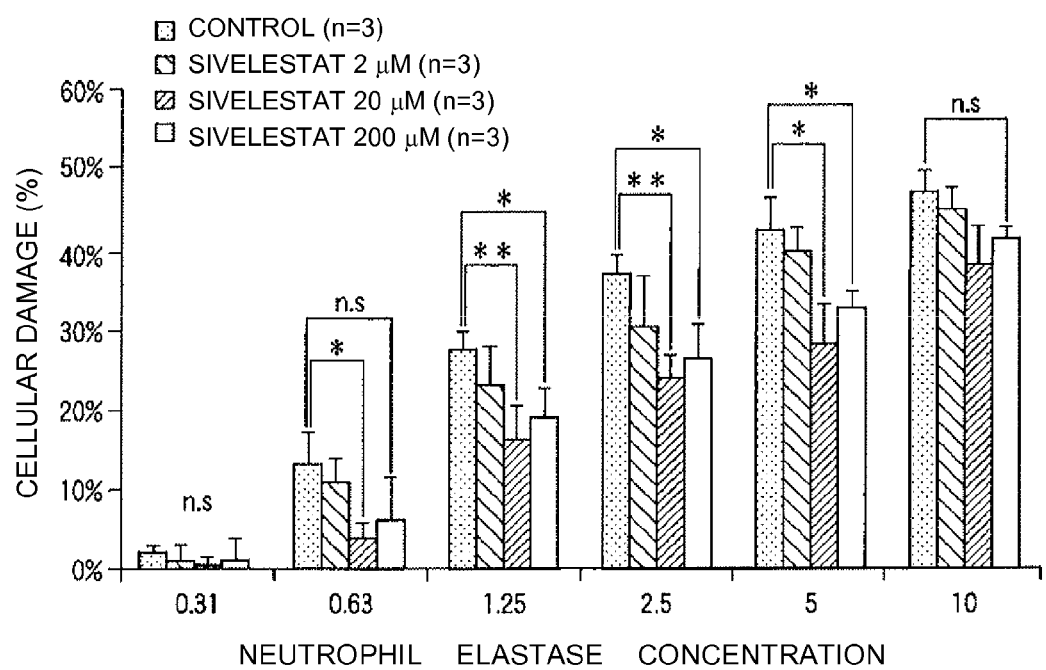
FIG. 3 is a graph showing the optimal concentration of a neutrophil elastase inhibitor.

The results are shown in FIG. 3. The vertical axis indicates the degree of cytotoxicity, and the high values mean the more damage of cells. The horizontal axis represents the concentration of neutrophil elastase. FIG. 3 shows that the higher concentration of neutrophil elastase causes the more damage of islet cells. At this time, when 2 µM, 20 µM, or 200 µM of sivelestat was added, the damage of islet cells was most suppressed in the presence of 20 µM of sivelestat. Thus, the optimal concentration of the neutrophil elastase inhibitor is suggested to be 20 µM.

Then, the present invention is specifically described with reference to Examples. These are only illustrative examples, and the present invention is not intended to be limited thereto.

Nine-week or older C57BL/6N mice (body weight: 20 to 22 g) were used in each of the methods for isolating islets described in Example 1 and Comparative Examples 1 to 3. An islet isolation method was adopted which involves only (4) the purification step after (3) the digestion step, omitting (1) the injection step and (2) the preservation step. The method was carried out by varying the ingredient of the preservation solution used in the digestion step in each example. The neutrophil elastase activity in each step was measured. The number, shape, size, and insulin-secreting ability of the islets obtained by these methods were measured. The details are described below.

Example 1

S-Kyoto

Elaspol (registered trade name, from Ono Pharmaceutical Co., Ltd., general name: sivelestat) was added to ET-Kyoto solution at the final concentration of 20 µM to prepare a protective solution (hereinafter referred to as S-Kyoto solution).

The above mice were each subjected to about 1-cm horizontal incision of the skin in the lower abdominal region under anesthesia, followed by ventrotomy by the V-shaped incision of the muscular layer. Then, after displacing the small intestine and the large intestine out of the body, the anterior diaphragm was incised and the heart was incised with scissors for intrathoracic bleeding to death. The pancreatic duct was isolated and it was punctured with a syringe (with a 30 G needle) to inject about 3 to 5 ml of a solution in which the protective solution prepared above was added to the digestion enzyme, type IV collagenase, thereinto to swell the pancreas. The swollen pancreas was isolated from the duodenum, the small intestine, the large intestine, and the spleen and transferred to a 50-ml conical tube and cooled on ice, followed by placing the tube containing the pancreas in a 37° C. warm bath to start digestion. The digestion was promoted by incubating the tube in the warm bath for about 15 minutes. Thereafter, the protective solution at cool temperature was added to the tube containing the pancreas to make suspension; then the digestion was terminated. In addition, the suspension containing the pancreatic tissue was washed and concentrated by a centrifugation operation. Finally, the above protective solution was added to the purification solution, OptiPrep (from Axis-Shield plc, general name: iodixanol solution), as a purification step to prepare 25%, 22.5%, 20%, and 11.1% solutions, and the respective concentrations of the solutions were superposed to form a non-continuous density gradient. Then, the collected suspension containing the pancreatic tissue was added thereto, which was then centrifuged to collect a fraction containing islets for purification.

Comparative Example 1

ET-Kyoto

Comparative Example 1 adopted ET-Kyoto solution (containing no Elaspol) in place of the protective solution of Example 1. As a purification solution, ET-Kyoto solution added with OptiPrep was adopted. Other operations were performed as in Example 1.

Comparative Example 2

M-Kyoto

In place of the protective solution of Example 1, Comparative Example 2 used ET-Kyoto solution added with Miraclid (registered trade name, from Mochida Pharmaceutical Co., Ltd., general name: urinastatin) (hereinafter referred to as M-Kyoto). As the purification solution, ET-Kyoto solution added with OptiPrep and Miraclid was adopted. To 1 L of ET-Kyoto solution was added 100,000 units of Miraclid. Other operations were performed as in Example 1.

Comparative Example 3

UW

Comparative Example 3 adopted Viaspan (registered trade name, from Bristol-Myers Squibb, general name: UW solution) in place of the protective solution of Example 1. Viaspan was adopted for the purification solution. Other operations were performed as in Example 1.

(1) Period of Neutrophil Elastase Activation and Solutions Used

The activity of neutrophil elastase was measured in each step of the isolation method performed in Example and Comparative Examples. Measurements were performed at 4 timepoints: "before digestion", "after digestion", "before purification", and "after purification". As used herein, the "before digestion" refers to a state in which collagenase, having the effect of breaking down pancreas, was injected into the pancreatic duct to swell the pancreas, that is, after the enzyme injection step and before the digestion initiation step in the invention of the present application. The "after digestion" refers to a state in which the collagenase was activated after swelling to break down the pancreas, followed by inactivating the collagenase to terminate the digestion, that is, after the digestion termination step and before the collection step in the invention of the present application. The "before purification" refers to a state in which the pancreatic tissue was washed after terminating the digestion, that is, after the collection step and before the purification step in the invention of the present application. The "after purification" refers to a state in which islets were isolated from the exocrine pancreatic tissue using a density gradient reagent, that is, after the purification step in the invention of the present application.

The specific measurement of neutrophil elastase activity was carried out by the following procedure. The supernatant of the suspension containing the pancreatic tissue was used as a measurement sample and incubated in a reaction solution containing a neutrophil elastase-specific substrate at 37° C. for 24 hours, followed by measuring the amount of p-nitroanilide released into the reaction solution using absorbance at a wavelength of 405 nm. At this time, N-methoxysuccinyl-Ala-Ala-Pro-Val-p-nitroanilide was used as the neutrophil elastase-specific substrate, and the amount of p-nitroanilide was calculated from a calibration curve prepared using known concentration of p-nitroanilide and defined as the neutrophil elastase activity.

Figure 4:
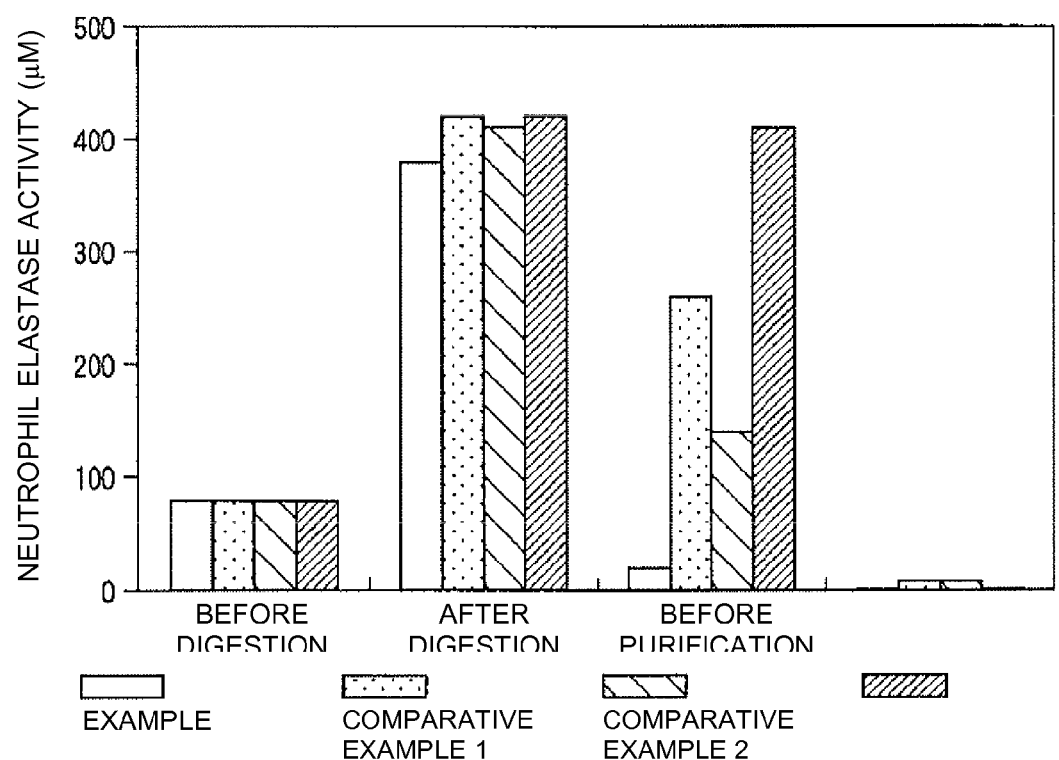
FIG. 4 is a graph showing neutrophil elastase activity in each step of the islet isolation method described in Example and Comparative Examples.

The results are shown in FIG. 4. All neutrophil elastase activities in Example 1 and Comparative Examples 1 to 3 were about 100 µM before digestion. All neutrophil elastase activities were similarly increased from 300 µM to 400 µM after digestion; however, they were decreased after purification and lower than those before digestion. The neutrophil elastase activity after digestion was lowest in Example 1, second-lowest in Comparative Example 2, and similarly highest in Comparative Examples 1 and 3. In FIG. 4, the increase of neutrophil elastase activity from before digestion to after digestion indicates that neutrophils were activated by the digestion of the pancreatic tissue. The neutrophil elastase activity before purification was lowest in Example 1, and this was followed by Comparative Example 2, Comparative Example 1, and Comparative Example 3. The lowest neutrophil elastase activity in Example 1 was probably due to the action of the neutrophil elastase inhibitor. In addition, when a variation in the value of neutrophil elastase activity is observed, the largest variation was evidenced after digestion and before purification, and the action of the neutrophil elastase inhibitor can be said to be most exerted after digestion.

The above results demonstrated that it was the protective solution of Example 1 that had the strongest effect of not sustaining the activity of neutrophil elastase and immediately suppressing it.

(3) IEQ, Isolation Index, Purity, and Pancreatic Islet Size Distribution

These indicators were calculated by measuring the number, the longest diameter, and the area of islets obtained by the methods described in Example 1 and Comparative Examples 1 to 3. IEQ is an abbreviation of islet equivalents and an international unit indicating the volume of islets, in which the volume of an islet having a diameter of 150 µm is defined as 1. The number of isolated islets was defined as the number obtained by taking 50 µL from 1 mL of a solution containing islet cells, measuring the number of the islets stained by dithizone, and multiplying the resultant number by 20. The longest diameter and the area of islets were measured by image analysis using a fluorescent microscope, VH Analyzer (KEYENCE CORPORATION). The isolation index was calculated using IEQ and the number of islets and using the calculation formula expressed by: isolation index=IEQ/the number of islets. The purity was calculated using the area obtained from the image analysis and using the calculation formula expressed by: purity=the area stained by dithizone/the total area. The islet size distribution was divided into size classes: 50 µm to 100 µm, 100 µm to 150 µm, 150 µm to 200 µm, 200 µm to 250 µm, 250 µm to 300 µm, 300 µm to 350 µm, and 350 µm or more, based on the major diameter of islets obtained by image analysis and the percentage of each distribution in the number of all islets was calculated.

Figure 5:
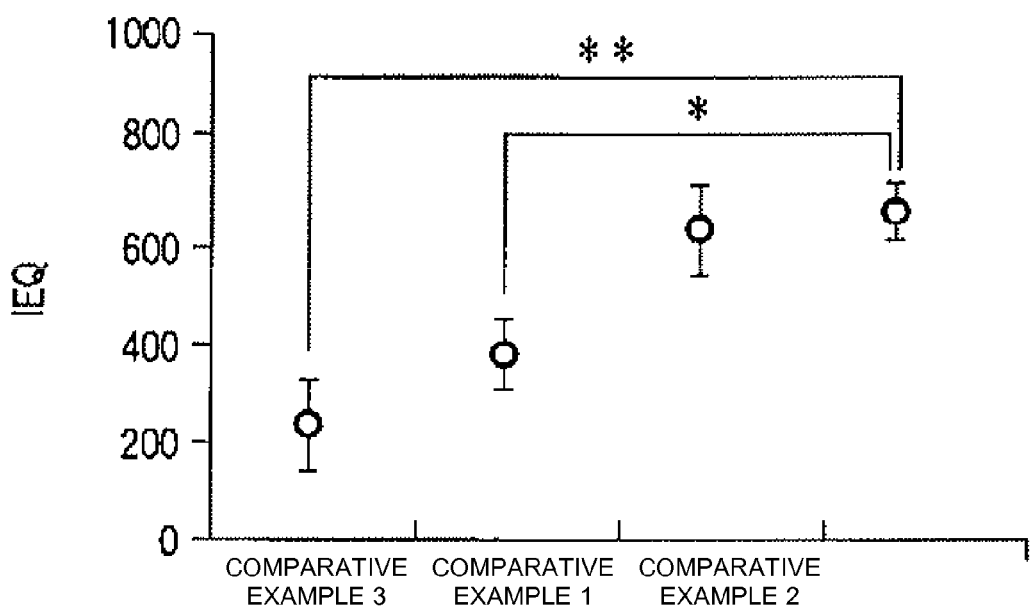
FIG. 5 is a graph showing IEQ (islet equivalent) of the islets obtained.

FIG. 5 shows the IEQ of the islets obtained. This shows that the IEQ thereof in Example 1 is significantly higher compared to that in Comparative Example 1 and in Comparative Example 3.

Figure 6:
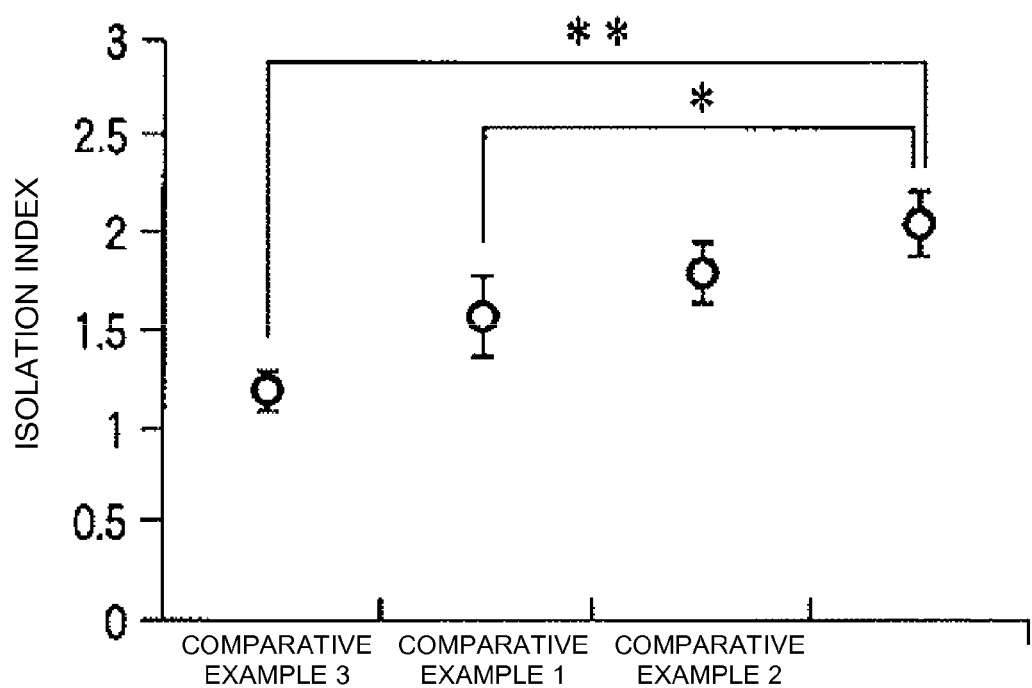
FIG. 6 is a graph showing the isolation index of the islets obtained.

FIG. 6 shows the isolation index of the islets obtained. This shows that the isolation index thereof in Example 1 is significantly higher compared to that in Comparative Example 1 and in Comparative Example 3.

Figure 7:
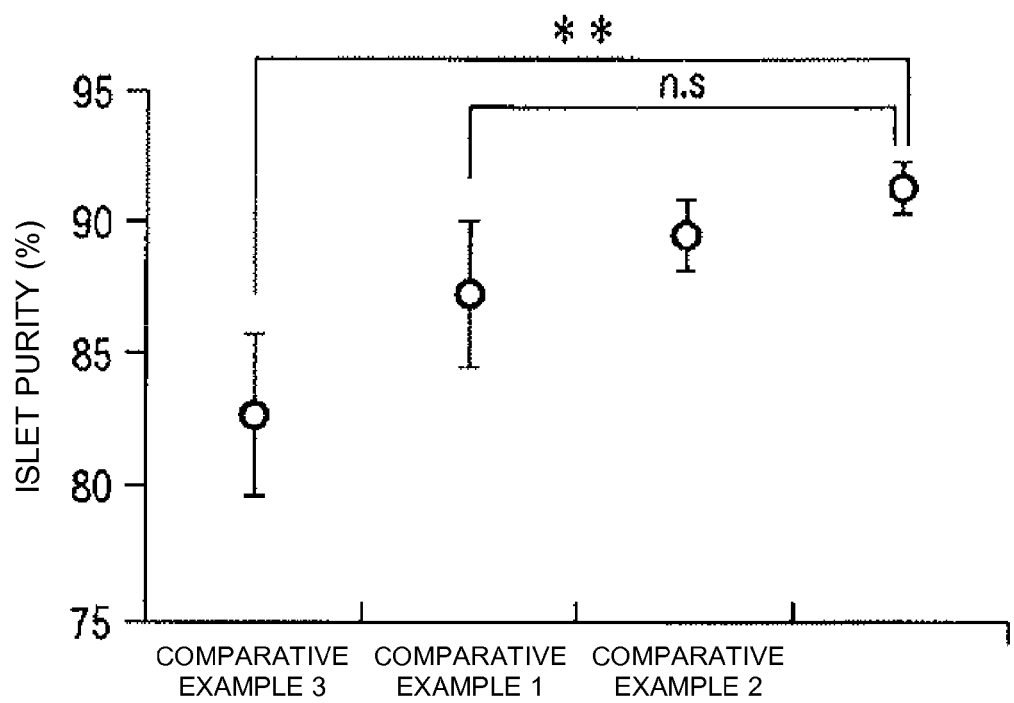
FIG. 7 is a graph showing the purity of the islets obtained.

FIG. 7 shows the purity of the islets obtained. This shows that the purity thereof in Example 1 is significantly higher compared to that in Comparative Example 3.

Figure 8:
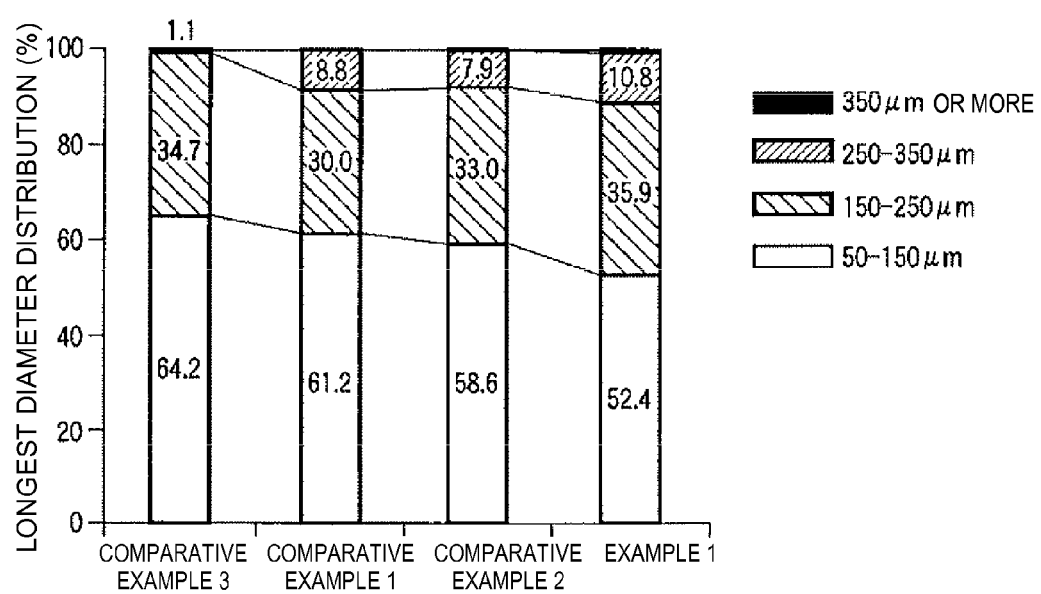
FIG. 8 is a graph showing the distribution of longest diameters of the islets obtained.

FIG. 8 shows the distribution of the diameter of the longest islets obtained. This shows that islets of 150 µm or less were fewer in number for Example 1 compared to those for Comparative Examples. In addition, islets of 250 µm to 350 µm were more in number for Example 1 compared to those for Comparative Examples and islets of 350 µm or more can be obtained for Example 1. It is only for Comparative Example 2 that islets of 350 µm or more could be obtained for other than Example; this also shows that large islets were obtained in high yields in Example compared to in Comparative Examples.

(4) Shape

Figure 9:
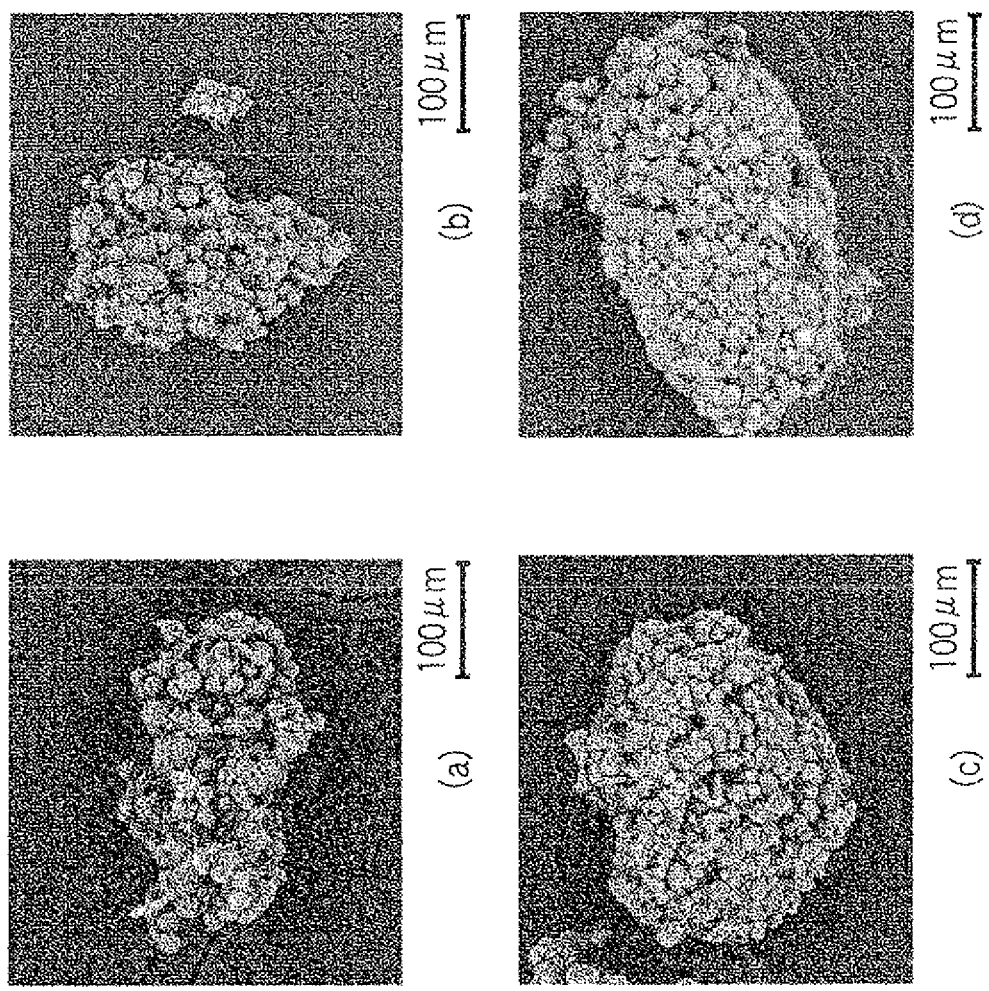
FIG. 9 is a series of photographs ((a) to (d)) showing electron photomicrographs of the islets obtained.

FIG. 9 shows photographs of the islets obtained. FIGS. 9(a) to 9(d) are photographs under an electron microscope. In FIG. 9, (a) shows Comparative Example 3, (b), Comparative Example 1, (c), Comparative Example 2, and (d), Example 1. This shows that the islets obtained in Example 1 each has good roundness, a dense structure, and a reduced broken-down tissue compared to the islets in Comparative Examples. The shapes of the islets obtained in Example 1 and Comparative Examples 1 to 3 were consistent with the results of the neutrophil elastase activity after digestion. Thus, in Example 1, the action of the neutrophil elastase inhibitor probably suppressed the damage of the pancreatic tissue.

(5) Stimulation Index

Figure 10:
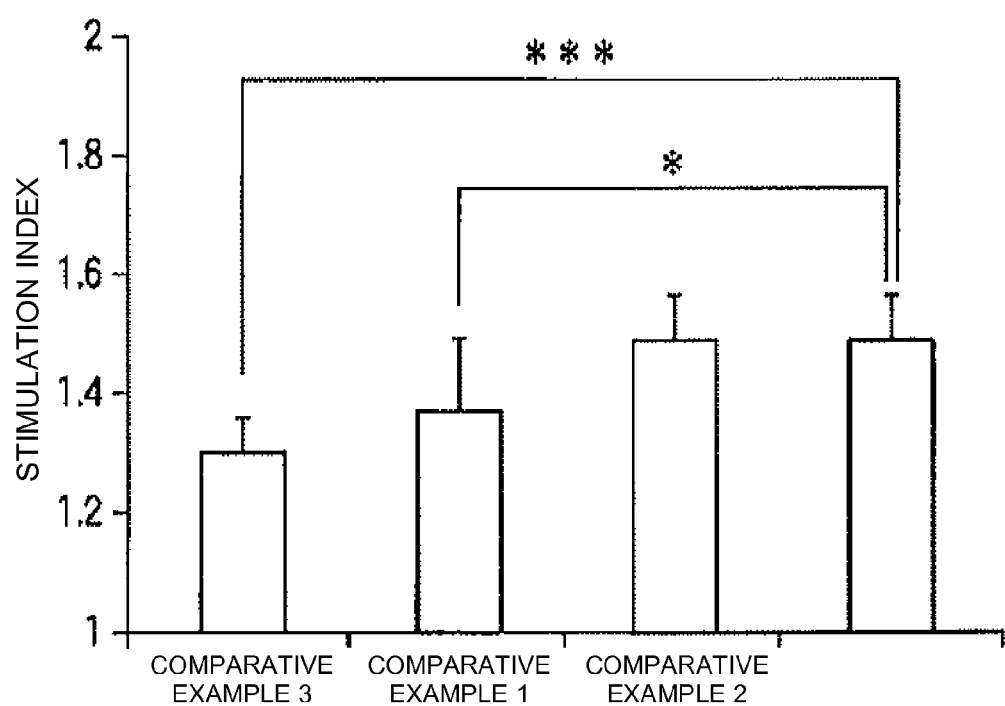
FIG. 10 is a graph showing the stimulation index of the islets obtained.
Figure 2:
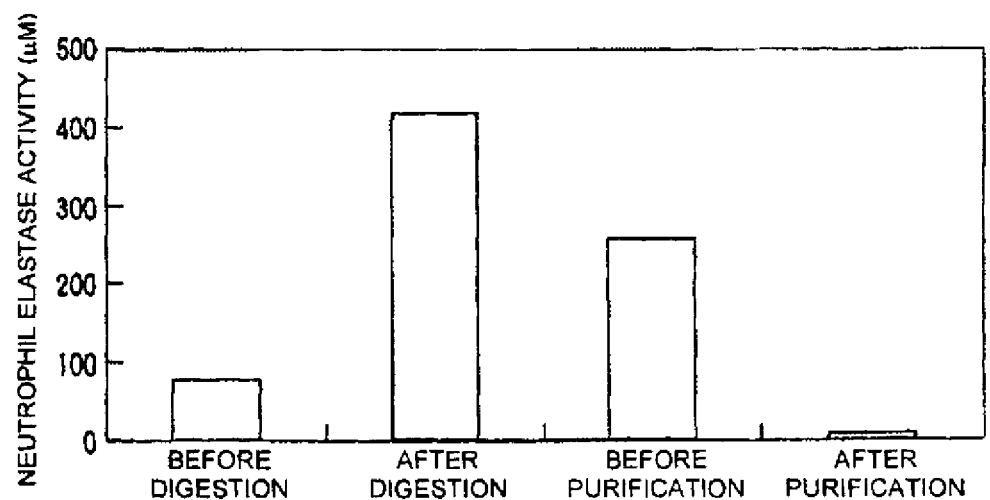
Figure 3:
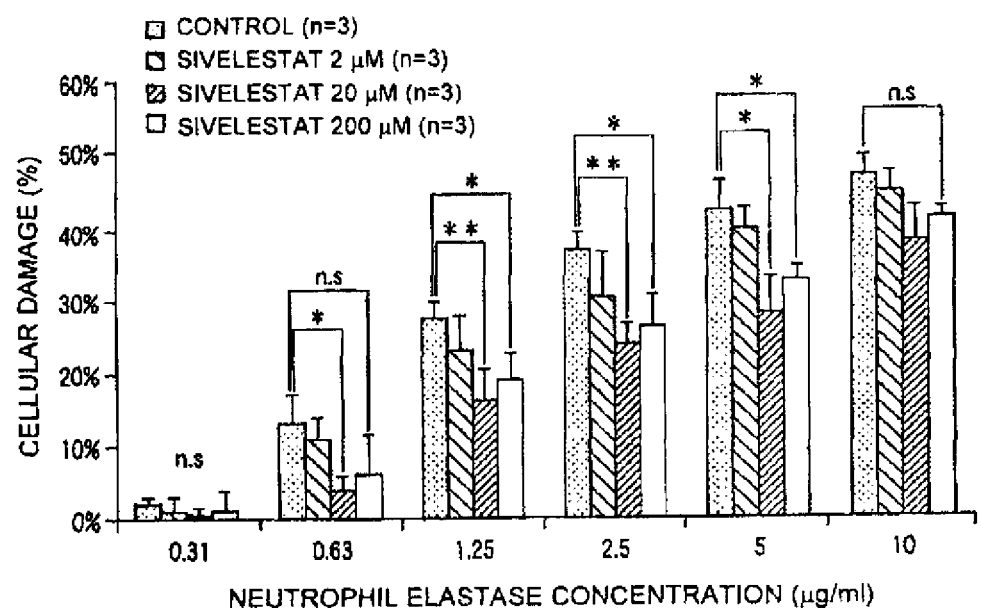
Figure 4:
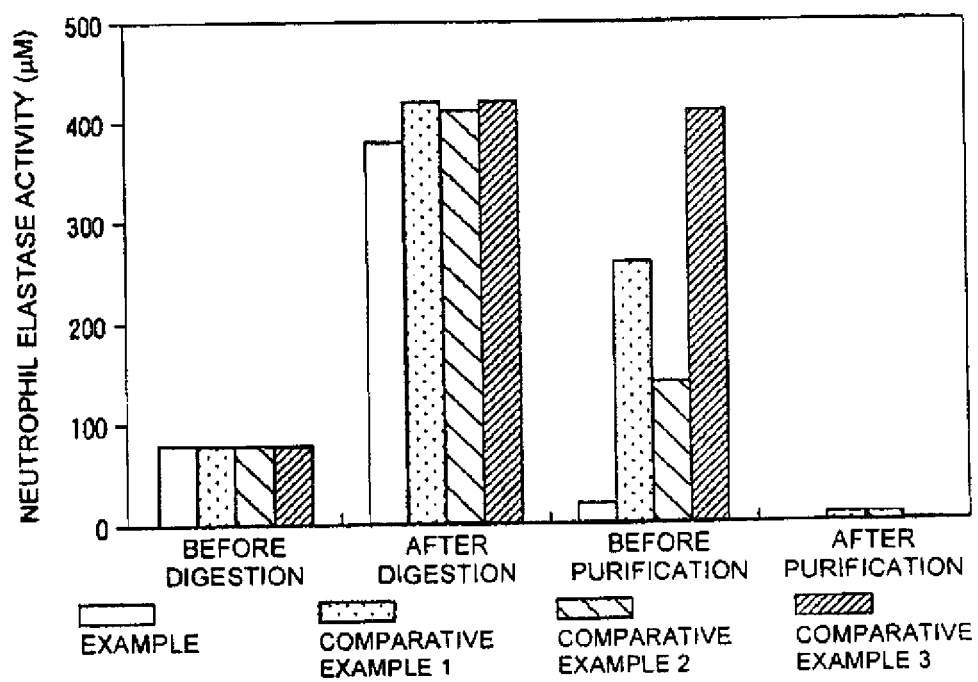
Figure 5:
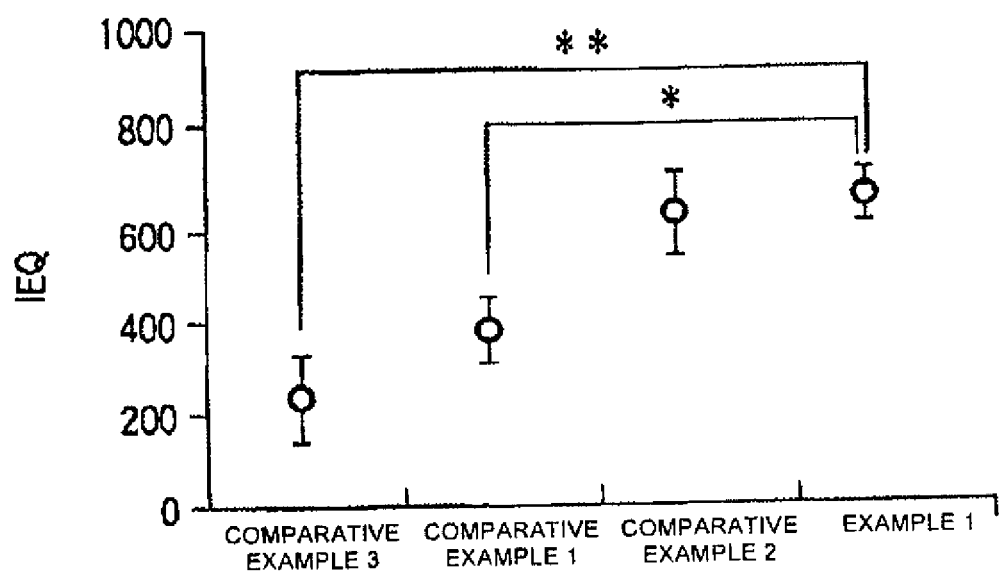
Figure 6:
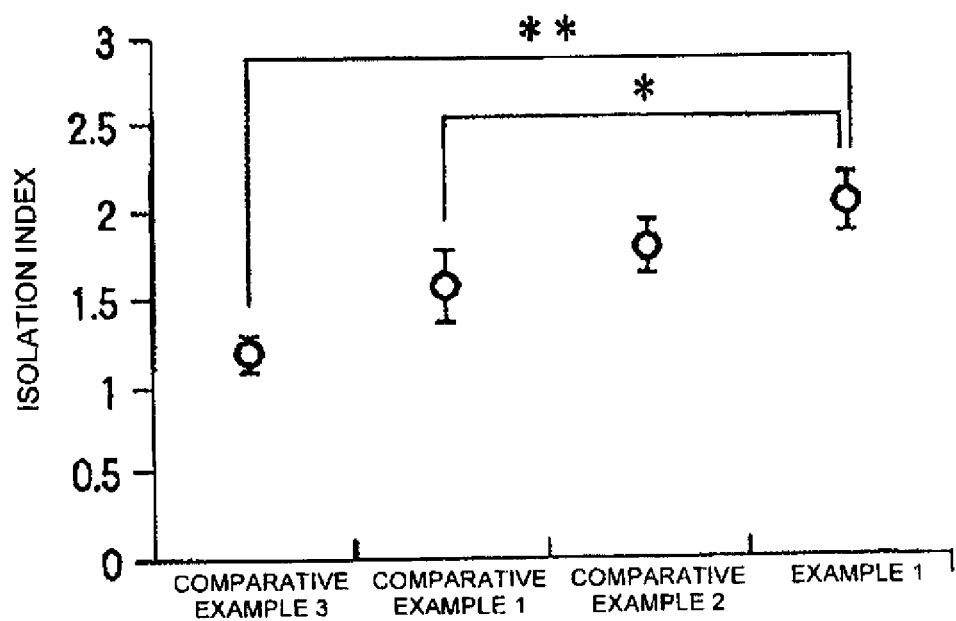
Figure 7:
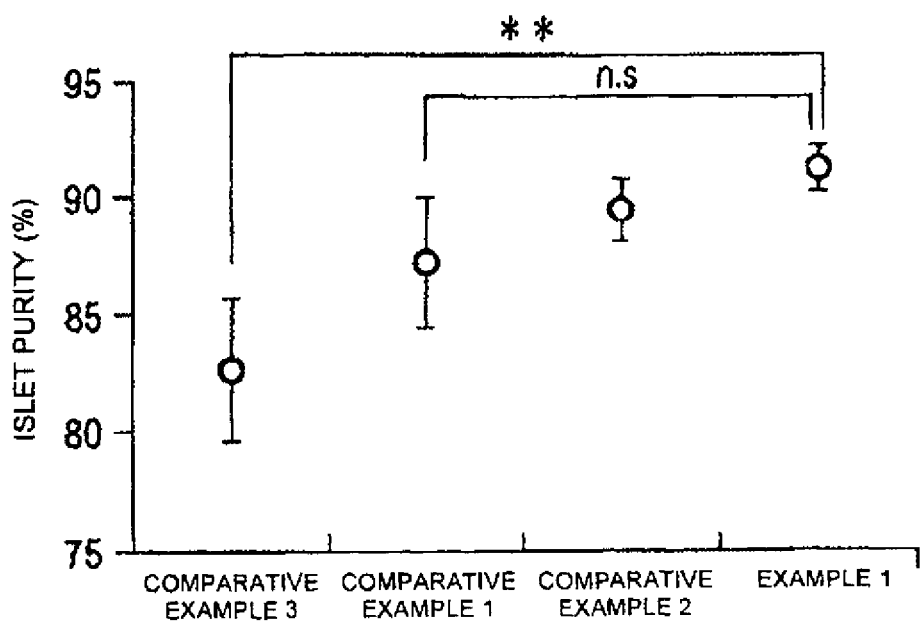
Figure 10:
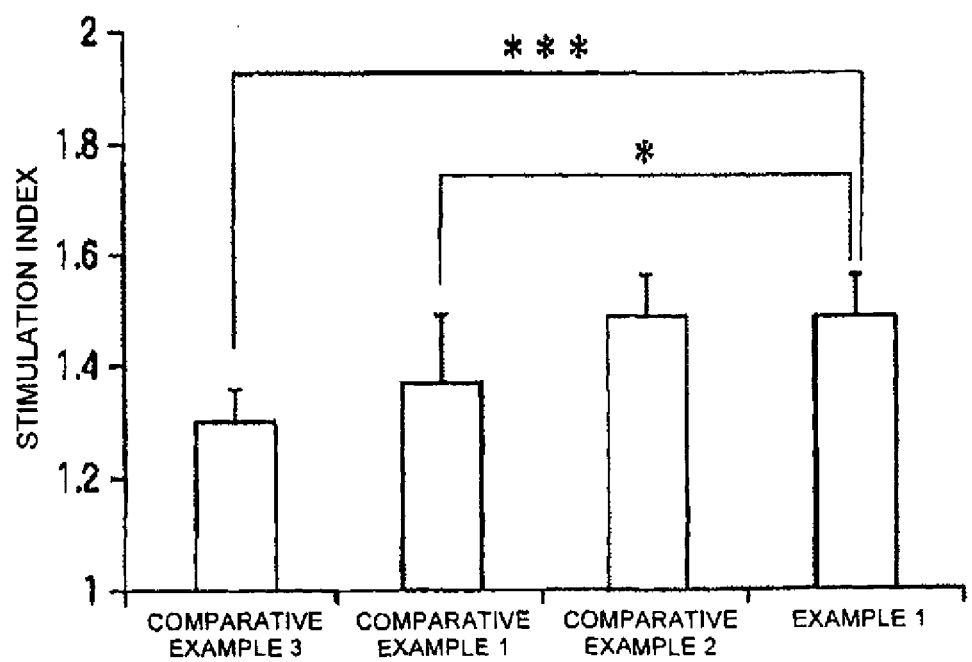

FIG. 10 shows the stimulation index of the islets obtained. As used herein, the stimulation index is an indicator showing the secretory ability of the islets. The isolation of the islets was carried out using the same operation as in Example 1. Thirty each of the islets obtained in Example 1 and Comparative Examples 1 to 3 were cultured under the condition of 37° C. for 24 hours and then cultured under a condition of a low glucose concentration or a high glucose concentration for a determined time, followed by measuring the concentration of insulin in the supernatant. The stimulation index was calculated from the ratio between the abilities to secrete insulin in the low glucose concentration and the high glucose concentration. According to FIG. 10, the stimulation index was significantly higher in Example 1 than in Comparative Examples 1 and 3. This demonstrated that the islets obtained in Example 1 exhibited better insulin secretion responding to glucose stimulation than the islets obtained in Comparative Examples 1 and 3.

INDUSTRIAL APPLICABILITY

The islet isolation method of the present invention enables islets having shapes and sizes suitable for transplantation to be obtained in high yields and can be expected to be applied to the treatment of diabetes.

The present invention has been specifically described with reference to particular embodiments. However, it will be apparent to those skilled in the art that various changes and modifications may be made without departing from the spirit and scope of the present invention.

The present application is a National Stage application of PCT/JP2011/065997, filed Jul. 13, 2011, which claims priority from on Japanese Patent Application No. 2010-159053 filed Jul. 13, 2010, the contents of which are incorporated herein by reference. All cited references are incorporated herein in their entirety.

The invention claimed is:

1. A method for isolating islets, comprising:
   a digestion step of breaking down an excised pancreas to provide pancreatic tissue, and
   a purification step of immersing the pancreatic tissue in a purification solution to provide islets,
   wherein the digestion step comprises:
   an enzyme injection step of injecting an enzyme solution containing a digestive enzyme into the inside of the pancreas;
   a digestion initiation step of activating the digestive enzyme;
   a digestion termination step of inactivating the digestive enzyme; and
   a collection step of collecting the broken down pancreatic tissue,
   wherein a neutrophil elastase inhibitor, provided that a case of it being a trypsin inhibitor is excluded, is added before the digestion initiation step so that the neutrophil elastase inhibitor is present in the inside of the pancreas at the time point of starting the digestion initiation step.

2. The method for isolating islets according to claim 1, further comprising before the digestion step an injection step of injecting a preservation solution into the pancreatic duct of an excised pancreas and/or a preservation step of immersing the pancreas in an immersion fluid for preservation.

3. The method for separating islets according to claim 2, wherein the preservation solution and the immersion fluid do not contain a neutrophil elastase inhibitor.

4. The method for isolating islets according to claim 1, wherein the addition of the neutrophil elastase inhibitor is performed by adding the neutrophil elastase inhibitor to the enzyme solution.

5. The method for isolating islets according to claim 1, wherein the addition of the neutrophil elastase inhibitor is performed by adding the neutrophil elastase inhibitor to the enzyme solution and the purification solution.

6. The method for isolating islets according to claim 2, wherein the addition of the neutrophil elastase inhibitor is performed by adding the neutrophil elastase inhibitor to all of the preservation solution, the immersion fluid, the enzyme solution, and the purification solution.

7. The method for isolating islets according to claim 4, wherein the concentrations of the neutrophil elastase inhibitor in the enzyme solution is 2 to 200 µM.

8. The method for isolating islets according to claim 2, wherein the addition of the neutrophil elastase inhibitor is performed by adding the neutrophil elastase inhibitor to the enzyme solution.

9. The method for isolating islets according to claim 3, wherein the addition of the neutrophil elastase inhibitor is performed by adding the neutrophil elastase inhibitor to the enzyme solution.

10. The method for isolating islets according to claim 2, wherein the addition of the neutrophil elastase inhibitor is performed by adding the neutrophil elastase inhibitor to the enzyme solution and the purification solution.

11. The method for isolating islets according to claim 3, wherein the addition of the neutrophil elastase inhibitor is performed by adding the neutrophil elastase inhibitor to the enzyme solution and the purification solution.

12. The method for isolating islets according to claim 8, wherein the concentration of the neutrophil elastase inhibitor in the enzyme solution is 2 to 200 µM.

13. The method for isolating islets according to claim 9, wherein the concentration of the neutrophil elastase inhibitor in the enzyme solution is 2 to 200 µM.

* * * * *

UNITED STATES PATENT AND TRADEMARK OFFICE
CERTIFICATE OF CORRECTION

PATENT NO. : 8,759,099 B2
APPLICATION NO. : 13/808390
DATED : June 24, 2014
INVENTOR(S) : Masahiro Tanemura et al.

It is certified that error appears in the above-identified patent and that said Letters Patent is hereby corrected as shown below:

In the Drawings

Figure 2, bottom right, after "BEFORE PURIFICATION", insert --AFTER PURIFICATION--. (attached)

Figure 3, bottom right, after "CONCENTRATION" insert --($\mu$G/ML)--. (attached)

Figure 4, bottom right, after "BEFORE PURIFICATION", insert --AFTER PURIFICATION--. (attached)

Figure 4, bottom right, after "COMPARATIVE EXAMPLE 2" insert --COMPARATIVE EXAMPLE 3--. (attached)

Figures 5, 6, 7 and 10, bottom right, after "COMPARATIVE EXAMPLE 2" insert --EXAMPLE 1--. (attached)

Signed and Sealed this
Fourth Day of November, 2014

Michelle K. Lee
*Deputy Director of the United States Patent and Trademark Office*